United States Patent
Kuzma et al.

(10) Patent No.: US 6,498,954 B1
(45) Date of Patent: Dec. 24, 2002

(54) APEX TO BASE COCHLEAR IMPLANT ELECTRODE

(75) Inventors: Janusz A. Kuzma, Englewood, CO (US); Thomas H. R. Lenarz, Hannover (DE)

(73) Assignee: Advanced Bionics Corporation, Sylmar, CA (US)

( * ) Notice: Subject to any disclaimer, the term of this patent is extended or adjusted under 35 U.S.C. 154(b) by 83 days.

(21) Appl. No.: 09/758,104

(22) Filed: Jan. 10, 2001

Related U.S. Application Data (60) Provisional application No. 60/176,427, filed on Jan. 14, 2000.

(51) Int. Cl.$^7$ ............................................. A61N 1/05
(52) U.S. Cl. .......................... 607/137; 607/57; 623/10
(58) Field of Search .............................. 607/55, 56, 57, 607/137, 115, 116; 623/10

(56) References Cited

U.S. PATENT DOCUMENTS

| | | | |
|---|---|---|---|
| 4,819,647 A | 4/1989 | Byers et al. | 128/642 |
| 5,545,219 A | 8/1996 | Kuzma | 623/10 |
| 5,645,585 A | 7/1997 | Kuzma | 623/10 |
| 5,653,742 A | 8/1997 | Parker et al. | 607/137 |
| 5,999,859 A | * 12/1999 | Jolly | 607/137 |
| 6,038,484 A | * 3/2000 | Kuzma | 607/137 |
| 6,074,422 A | 6/2000 | Berrang et al. | 623/10 |
| 6,112,124 A | * 8/2000 | Loeb | 607/137 |
| 6,119,044 A | 9/2000 | Kuzma | 607/137 |
| 6,125,302 A | 9/2000 | Kuzma | 607/137 |
| 6,144,883 A | 11/2000 | Kuzma | 607/137 |
| 6,149,657 A | 11/2000 | Kuzma | 606/129 |
| 6,151,526 A | 11/2000 | Tziviskos | 607/137 |
| 6,163,729 A | 12/2000 | Kuzma | 607/137 |
| 6,266,568 B1 | * 7/2001 | Mann et al. | 607/137 |
| 6,321,125 B1 | * 11/2001 | Kuzma | 607/137 |

FOREIGN PATENT DOCUMENTS

| | | |
|---|---|---|
| WO | 0045618 | 3/1997 |
| WO | 9710784 | 3/1997 |
| WO | 0064529 | 11/2000 |
| WO | 0071063 | 11/2000 |

* cited by examiner

*Primary Examiner*—Ira S. Lazarus
*Assistant Examiner*—Kathryn S. O'Malley
(74) *Attorney, Agent, or Firm*—Bryant R. Gold (57) ABSTRACT

An implantable electrode assembly includes a leading section attached to the distal end of an electrode array. The electrode array has electrodes spaced along its length. Cochleostomies are drilled at both the base and apex of the cochlea. The leading section is inserted through the basal cochleostomy and promoted to the apical cochleostomy. A forward end of the leading section is then pulled through the apical cochleostomy, which causes the electrode array to be pulled into the cochlea. A depth marker on the electrode array indicates complete insertion. The leading section is detached from the electrode array and the electrode array is placed in tension by gently pulling both ends, which tension causes the electrode array to hug the modiolar wall of the cochlea. Wedges may be inserted at both cochleostomies to maintain the electrode array in tension.

16 Claims, 8 Drawing Sheets

APEX TO BASE COCHLEAR IMPLANT ELECTRODE

This application claims the benefit of U.S. Provisoinal Patent Application Ser. No. 60/176,427, filed Jan. 14, 2000, which application is incorporated herein by reference.

BACKGROUND OF THE INVENTION

The present invention relates to implantable stimulation devices, e.g., cochlear prosthesis used to electrically stimulate the auditory nerve, and more particularly to an electrode array designed to provide focused electrical stimulation along the entire length of the cochlea (i.e., from base to apex,) and a method of insertion of the electrode array into the cochlea providing a snug fit against the modiolus.

Hearing loss, which may be due to many different causes, is generally of two types: conductive and sensorineural. Of these, conductive hearing loss occurs where the normal mechanical pathways for sound to reach the hair cells in the cochlea are impeded, for example, by damage to the ossicles. Conductive hearing loss may often be helped by use of conventional hearing aids, which amplify sound so that acoustic information does reach the cochlea and the hair cells. Some types of conductive hearing loss are also amenable to alleviation by surgical procedures.

In many people who are profoundly deaf, however, the reason for their deafness is sensorineural hearing loss. This type of hearing loss is due to the absence or the destruction of the hair cells in the cochlea which are needed to transduce acoustic signals into auditory nerve impulses. These people are unable to derive any benefit from conventional hearing aid systems, no matter how loud the acoustic stimulus is made, because their mechanisms for transducing sound energy into auditory nerve impulses have been damaged. Thus, in the absence of properly functioning hair cells, there is no way auditory nerve impulses can be generated directly from sounds.

To overcome sensorineural deafness, numerous cochlear implant systems—or cochlear prosthesis—have been developed which seek to bypass the hair cells in the cochlear by presenting electrical stimulation to the auditory nerve fibers directly, leading to the perception of sound in the brain and an at least partial restoration of hearing function. The common denominator in most of these cochlear prosthesis systems has been the implantation, into the cochlea, of electrodes which are responsive to a suitable external source of electrical stimuli and which electrodes are intended to transmit those stimuli to the ganglion cells and thereby to the auditory nerve fibers.

A cochlear prosthesis operates by direct electrical stimulation of the auditory nerve cells, bypassing the defective cochlear hair cells that normally transduce acoustic energy into electrical activity in such nerve cells. In addition to stimulating the nerve cells, the electronic circuitry and the electrode array of the cochlear prosthesis perform the function of separating the acoustic signal into a number of parallel channels of information, each representing the intensity of a narrow band of frequencies within the acoustic spectrum. Ideally, each channel of information would be conveyed selectively to the subset of auditory nerve cells that normally transmitted information about that frequency band to the brain. Those nerve cells are arranged in an orderly tonotopic sequence, from high frequencies at the basal end of the cochlear spiral to progressively lower frequencies towards the apex, and ideally the entire length of the cochlea would be stimulated to provide a full frequency range of hearing. In practice, this ideal is not achieved because of the anatomy of the cochlea which decreases in diameter from the base to the apex, and exhibits variations between patients. Because of these difficulties, known electrodes can only be promoted to the second turn of the cochlea at best.

Over the past several years, a consensus has generally emerged that the scala tympani, one of the three parallel ducts that, in parallel, make up the spiral-shaped cochlea, provides the best location for implantation of an electrode array used with a cochlear prosthesis. The electrode array to be implanted in this site typically consists of a thin, elongated, flexible carrier containing several longitudinally disposed and separately connected stimulating electrode contacts, perhaps 6–30 in number. Such electrode array is pushed or inserted into the scala tympani duct to a depth of about 20–30 mm via a surgical opening made in the round window at the basal end of the duct. During use, electrical current is passed into the fluids and tissues immediately surrounding the individual electrical contacts in order to create transient potential gradients that, if sufficiently strong, cause the nearby auditory nerve fibers to generate action potentials. The auditory nerve fibers arise from cell bodies located in the spiral ganglion, which lies in the bone, or modiolus, adjacent to the scala tympani on the inside wall of its spiral course. Because the density of electrical current flowing through volume conductors such as tissues and fluids tends to be highest near the electrode contact that is the source of such current, stimulation at one contact site tends to activate selectively those spiral ganglion cells and their auditory nerve fibers that are closest to that contact site. Thus, there is a need for the electrode contacts to be positioned as close to the ganglion cells as possible. This means, in practice, that the electrode array, after implant, should preferably hug the modiolar wall, and that the individual electrode contacts of the electrode array should be positioned on or near that surface of the electrode array which is closest to the modiolar wall.

In order to address the above need, it is known in the art to make an intracochlear electrode array that includes a spiral-shaped resilient carrier which generally has a natural spiral shape so that it better conforms to the shape of the scala tympani. See, e.g., U.S. Pat. No. 4,819,647. The '647 U.S. patent is incorporated herein by reference.

It is also known in the art, as shown in applicant's prior patents, U.S. Pat. Nos. 5,545,219 and 5,645,585, to construct an electrode carrier from two initially straight members, a rod-like electrode carrier and a flexible rod-like positioning member. As shown in these patents, the two members extend in substantially parallel relation to and closely alongside each other, but are connected to each other only at their respective leading and trailing end regions. After implant, a pushing force is applied to the positioning member so that it is forced to assume an outwardly arched configuration relative to the electrode carrier, thereby forcing the electrode carrier into a close hugging engagement with the modiolus, thereby placing the electrode contacts of the electrodes in as close a juxtaposition to the cells of the spiral ganglion as possible. The '219 and '585 U.S. patents are also incorporated herein by reference.

Unfortunately, while the electrode array taught in the above-referenced –219 and '585 patents has the right idea, i.e., to force the electrode carrier into a close hugging engagement with the modiolus, it does so only through application of an additional pushing force which is applied to an electrode structure after it is already fully inserted into the cochlea. Such additional pushing force may easily cause damage to the delicate scala tympani. Moreover, the entire electrode array may twist during the insertion process, or when the additional pushing force is applied, thereby causing the electrode contacts to twist and/or be forced away from the modiolus, rather than in a hugging relationship therewith.

It is thus seen that improvements are still needed in cochlear electrodes, particularly to provide an electrode array that extends the length of the cochlea and that better assures that the electrode contacts assume a close hugging relationship with the modiolus.

SUMMARY OF THE INVENTION

The present invention addresses the above and other needs by providing an implantable cochlear electrode array and leading section that permits the electrode array to first be gently promoted through the entire length of the cochlea, thereby providing stimulation of the entire range of nerves, and then permits the electrode array to be gently pulled from both ends to position the electrode array against the modiolus, or the inner wall of the scala tympani, to better stimulate the nerve fibers.

In accordance with one aspect of the invention, there is provided a leading section that may be easily promoted through the entire length of the cochlea. The leading section contains no electrical components and is not a permanent part of the implant. After the leading section is in place it is used to gently pull the electrode array through the cochlea.

It is thus a feature of the present invention to provide a method of positioning the electrode array against the inner wall of the scala tympani. After pulling the electrode array through the scala tympani, the electrode array is positioned by gently pulling from both ends causing the electrode array to hug the inner wall of the scala tympani.

It is a further feature of the invention to provide wedging positioners that are inserted into each cochleostomy to fix the position of the electrode array following the insertion and positioning of the electrode array.

It is another feature of the invention to provide a method of electrode array insertion that advantageously requires only a gentle pulling force to properly position the electrode array, thus minimizing potential damage to the scala tympani.

In accordance with a first embodiment of the invention, the electrode array and leading section are manufactured as a single electrode assembly. The forward end of the leading section is inserted through a cochleostomy at the basal end of the cochlea and promoted through the cochlea. The forward end of leading section is then grabbed by a micro hook inserted through a second cochleostomy at the apical end of the cochlea and the forward end is pulled through the second cochleostomy. The leading section is then gently pulled through the second cochleostomy and the electrode array is fed through the first cochleostomy. When the electrode array is in the correct position within the cochlea, the ends of the electrode assembly emerging through the cochleostomies are gently pulled to seat the electrode array against the modiolus (or synonymously against the inner wall of the scala tympani.) Wedges are inserted at each cochleostomy to hold the electrode array in place, and the leading section is severed from the electrode array.

In accordance with an alternate embodiment of the invention, the electrode array and the leading section are separate detachable pieces that connect to form the electrode assembly. Additionally, the alternative leading section has an attaching end with a hoop, and the alternative electrode array has a forward end with a hook.

In the second embodiment the attaching end is fed through the apical cochleostomy. When the attaching end the reaches the basal cochleostomy, it is extracted using a micro hook. Then the hook on the electrode array is attached to the loop on the leading section, and the leading section is withdrawn pulling the electrode array into position within the cochlea. The electrode array is then gently pulled as in the first embodiment to seat the electrode array against the modiolus, i.e., against the inner wall of the scala tympani. Wedges are inserted at each cochleostomy to hold the electrode array in place, and the leading section is detached and discarded.

It is an additional feature that an non-tapered electrode array may be used in accordance with the present invention. When such non-tapered electrode array is used, the insertion process may be from either end of the cochlea.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

The materials from which the leads and electrode arrays of the present invention are made, for all the embodiments disclosed herein and any variations thereof, may be any suitable material as is known in the art, or as is subsequently developed. In general, the conductive electrode contacts and wires connected thereto are made from platinum or a platinum alloy or other suitable bio-compatible metals. The carrier in which the wires and electrodes are embedded may be made from Silastic silicone plastic, silicone rubber, LSR-70, or an equivalent bio-compatible material. The leads and electrode arrays are typically made using a suitable molding process, e.g., as disclosed in U.S. Pat. No. 4,819,647, previously incorporated herein by reference.

Figures 1A, 1B:
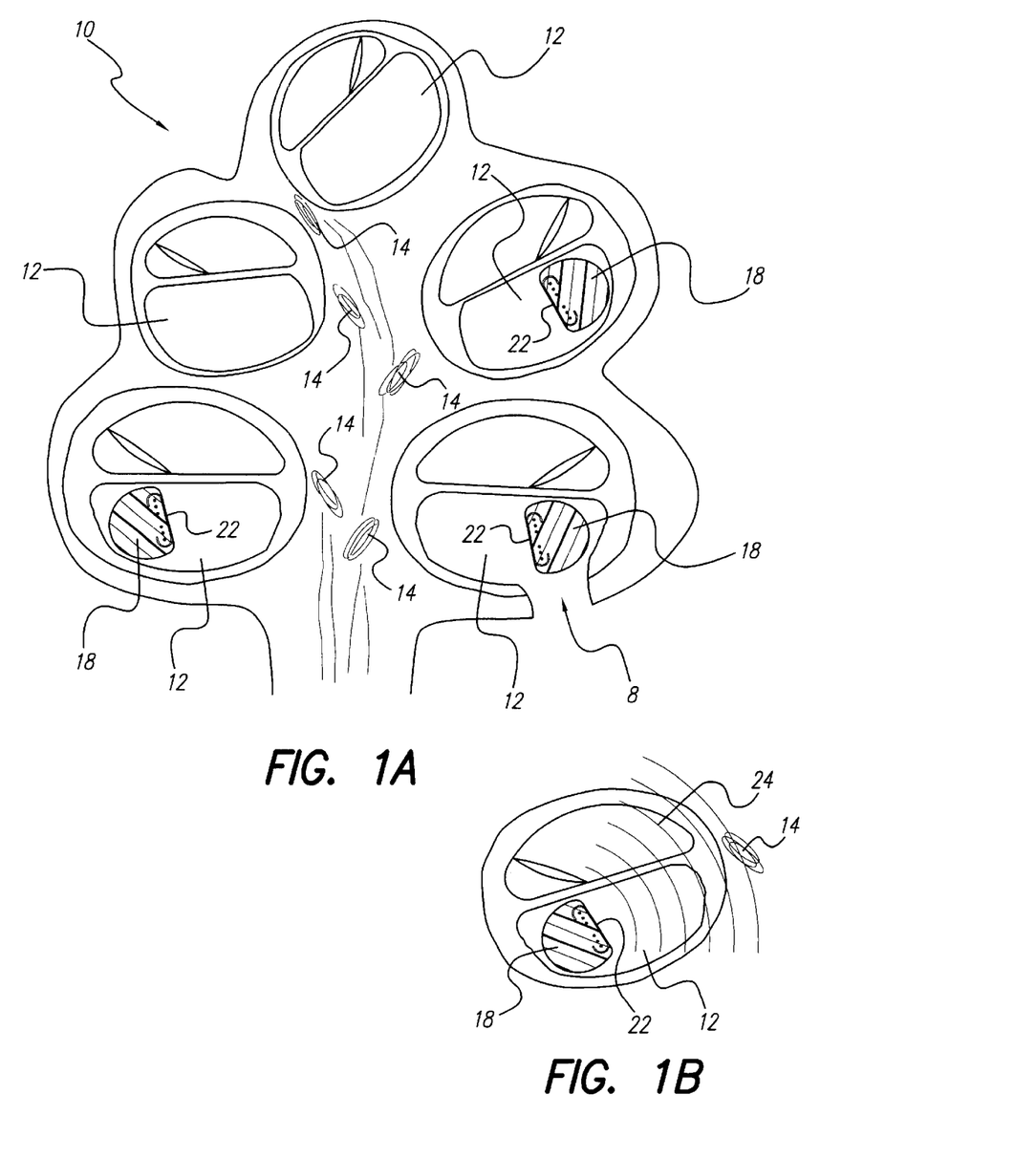
FIG. 1A depicts a cross-sectional view of the spiraling cochlea and illustrates the typical electrode array placement within the scala tympani of the cochlea using known, insertion methods.
FIG. 1B shows the relationship of the electrode to the ganglion cells that exists from a, known insertion such as is present in FIG. 1A.

Turning to FIG. 1A, a cross-sectional drawing illustrating the turns of spiraling cochlea 10 with an implanted electrode array 18 inserted therein. A typical cochlea has about 1½ to 2 turns, although this may vary from patient to patient. The cochlea 10 comprises three ducts. The implantable cochlear electrode array is generally positioned in the scala tympani 12 as shown. The use of known electrode arrays and known insertion methods through a basal cochleostomy 8 result in the array lying near the outside radius of the scala tympani 12. The electrode array is generally implanted within the cochlea 10 by gently feeding the electrode array 18 through the basal cochleostomy 8. As a natural result of this method the electrode array 18 tends to move to the outside of the scala tympani 12.

Now turning to FIG. 1B, the relationship of the electrodes 22 to the ganglion cells 14 resulting from an insertion as illustrated in FIG. 1A is shown in greater detail. When an electrical potential is applied to the electrode 22, electrical current flows from the electrode 22 through conductive body fluids and tissues as guided by electrical field 24. In general the electrical field 24 spreads spherically out from the electrode 22. The electrical current and the electrical field 24 stimulates the ganglion cells 14 resulting in the perception of sound by the patient. A larger current and higher source level for the electrical field 24 is required that would otherwise be needed because of the separation of the ganglion cell 14 from the electrode 22. Disadvantageously, the electrical field 24 and associated current are also spread over a greater volume, and thus may stimulate other ganglion cells that are not targeted for the stimulation. The net result of the separation of the electrode 22 from the ganglion cells 14 is the requirement for greater stimulation current, and undesirable collateral stimulation.

Figure 2:
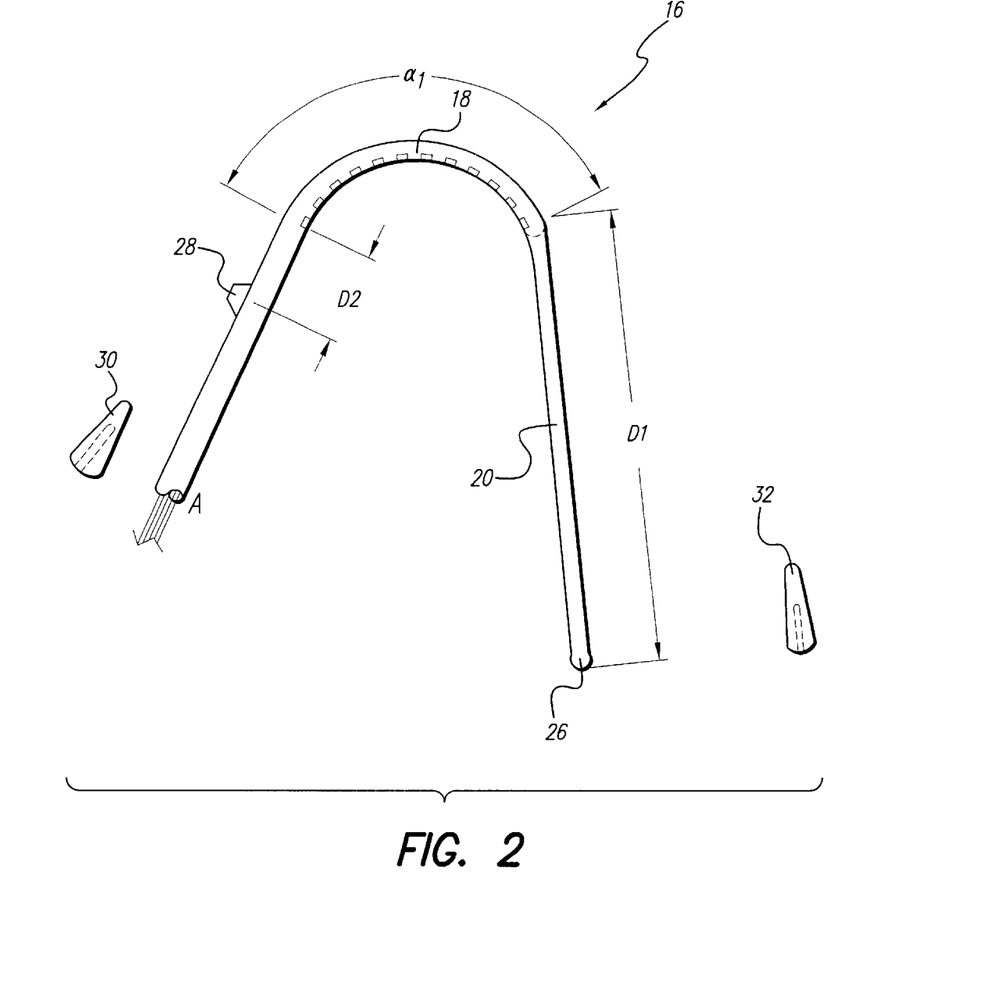
FIG. 2 depicts a first embodiment of an electrode assembly made in accordance with the present invention.

FIG. 2 shows an electrode assembly 16 made in accordance with the present invention. As seen in FIG. 2, the electrode assembly 16 includes an electrode array 18 and a leading section 20. The leading section 20 should be long enough to extend through the scala tympani 12 from the basal end of the scala tympani 12 to the apical end of the scala tympani 12, plus an additional length to aid in implantation, preferably a total length of about 35 mm. The leading section 20 is made from a very flexible material to aid in the leading section's promotion through the scala tympani 12. The forward end 26 of the leading section 20 is rounded to also aid in the leading section's promotion through the scala tympani 12. In the first embodiment, the leading section 20 and electrode array 18 are molded in one piece. The electrode array 18 is attached to the leading section 20 at the leading section's end opposite the leading end 26. The electrode array should be long enough to extend through the scala tympani 12 from the basal end of the scala tympani 12 to the apical end of the scala tympani 12 in order to allow stimulation of the entire range of ganglion cells. Additionally, the electrode array 18 may be slightly precurved to better fit the scala tympani 12. Approximately 5 mm from the base of the electrode array 18 (the end opposite the leading section), a depth marker 28 is provided to indicate the proper insertion depth of the electrode array 18. Additionally, a first wedge 30 is provided to fix the position of the implanted electrode array 18 at the basal end of the scala tympani, and a second wedge 32 is provided to fix the position of the implanted electrode array 18 at the apical end of the scala tympani.

Figure 3:
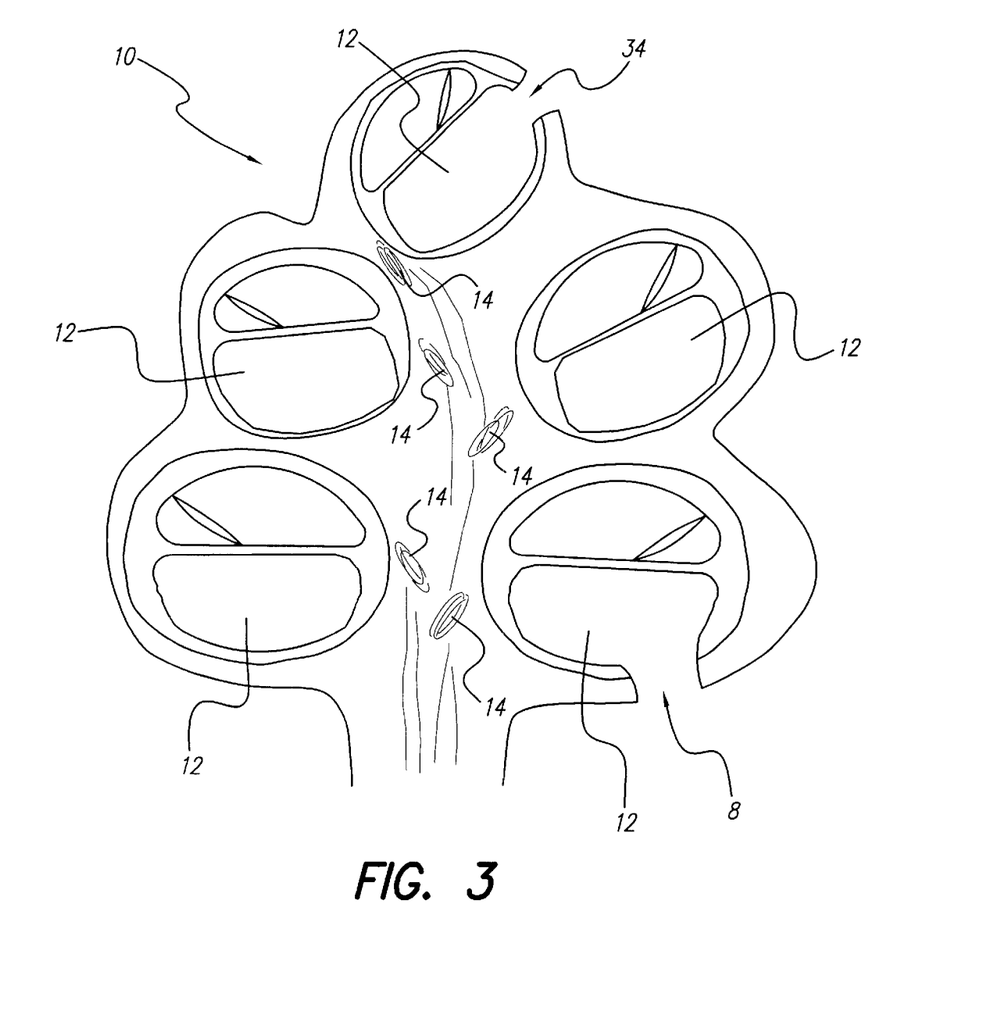
FIG. 3 shows a cross-sectional view of the spiraling cochlea and further depicts the locations of the basal and apical cochleostomies that are made as part of the insertion.

Turning to FIG. 3, the cochleostomies required by the present invention are shown. A basal cochleostomy 8 is required, as is known in the art. Additionally, an apical cochleostomy 34 is required by the present invention. The basal cochleostomy 8 is drilled near the round window of the cochlea 10. The apical cochleostomy 34 is drilled at or near the apex of the cochlea.

Figure 4:
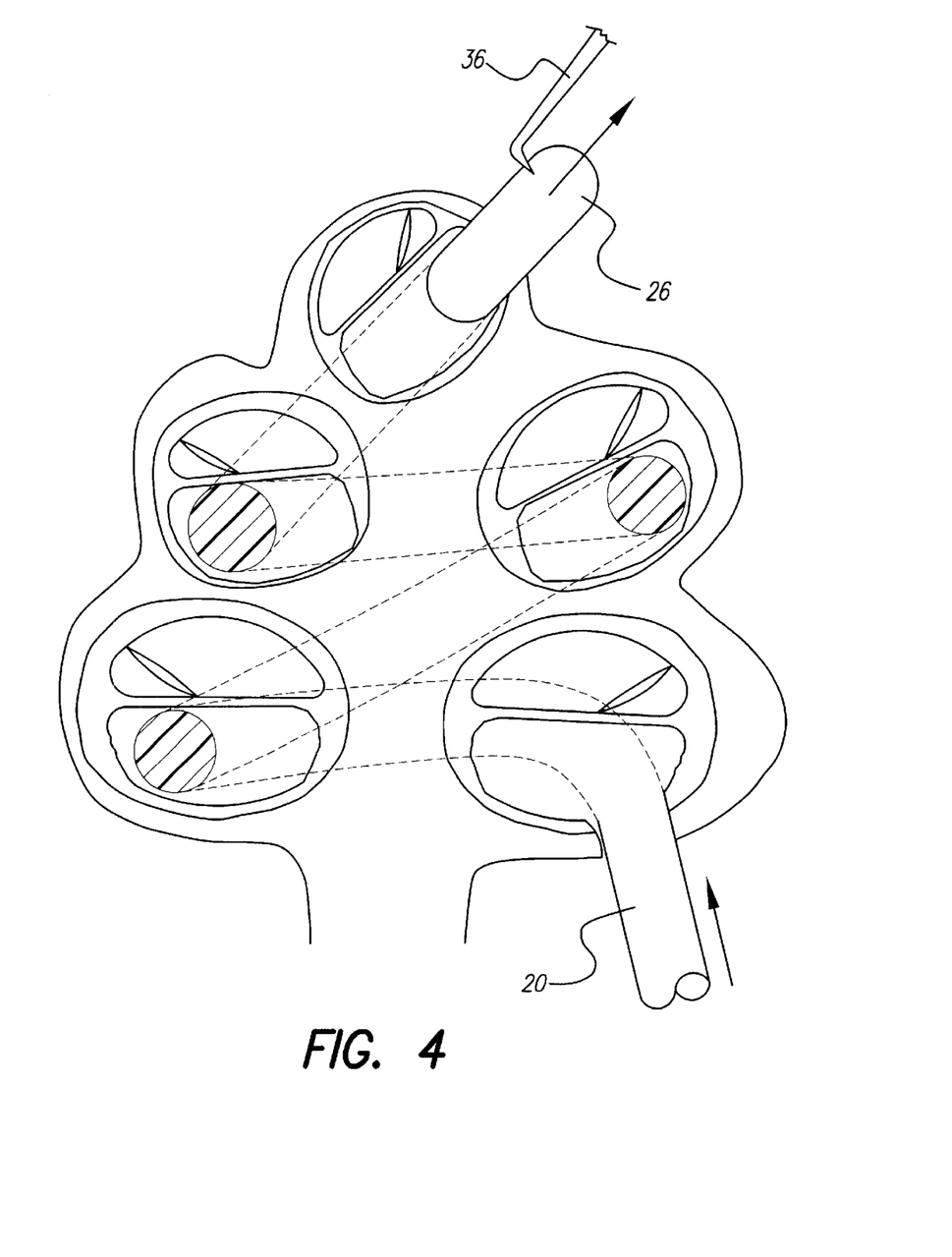
FIG. 4 illustrates the insertion of the leading section of the electrode array through the cochlea.

The initial insertion of the leading section 20 into the scala tympani 12 is shown in FIG. 4. In a preferred embodiment, the leading section is inserted through the basal cochleostomy 8 and gently promoted though the length of the scala tympani 12 to the apical cochleostomy 34. The small diameter, round cross section, and flexibility of the leading section 20 all contribute to enabling the promotion of the leading section 20 through the entire length of the scala tympani 12 without difficulty. When the leading section 20 reaches the apical cochleostomy 34, a micro hook 36, or equivalent, is used to grab the forward end 26 of the leading section 20 and to extract the forward end 26 through the apical cochleostomy 34.

Figure 5:
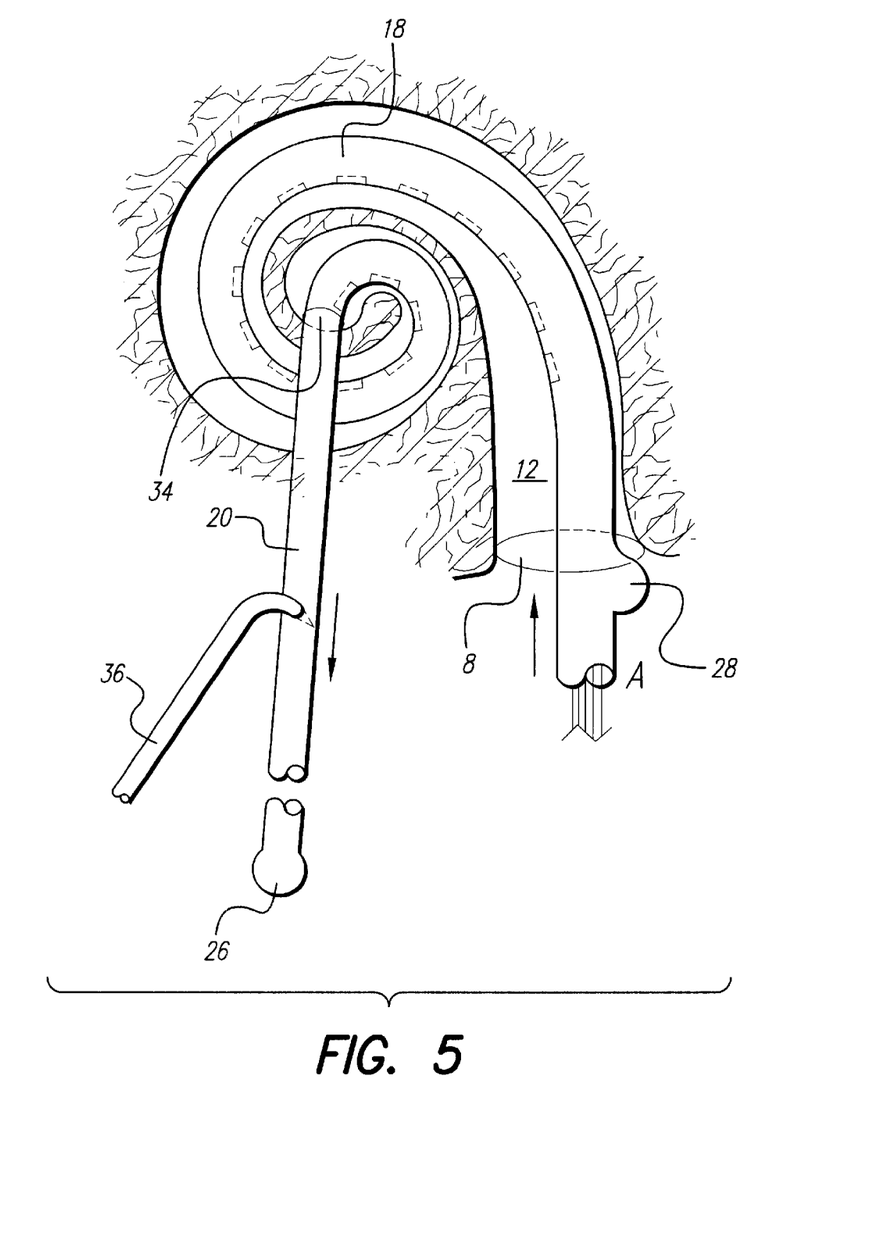
FIG. 5 is a sectional view of the cochlea from a different view and depicts the pulling of the electrode array through the cochlea.

Next, the leading section 20 is gently pulled through the apical cochleostomy 34 and the electrode array 18 is concurrently fed through the basal cochleostomy 8, until the depth marker 28 reaches the basal cochleostomy 8, as shown in FIG. 5.

Figure 6:
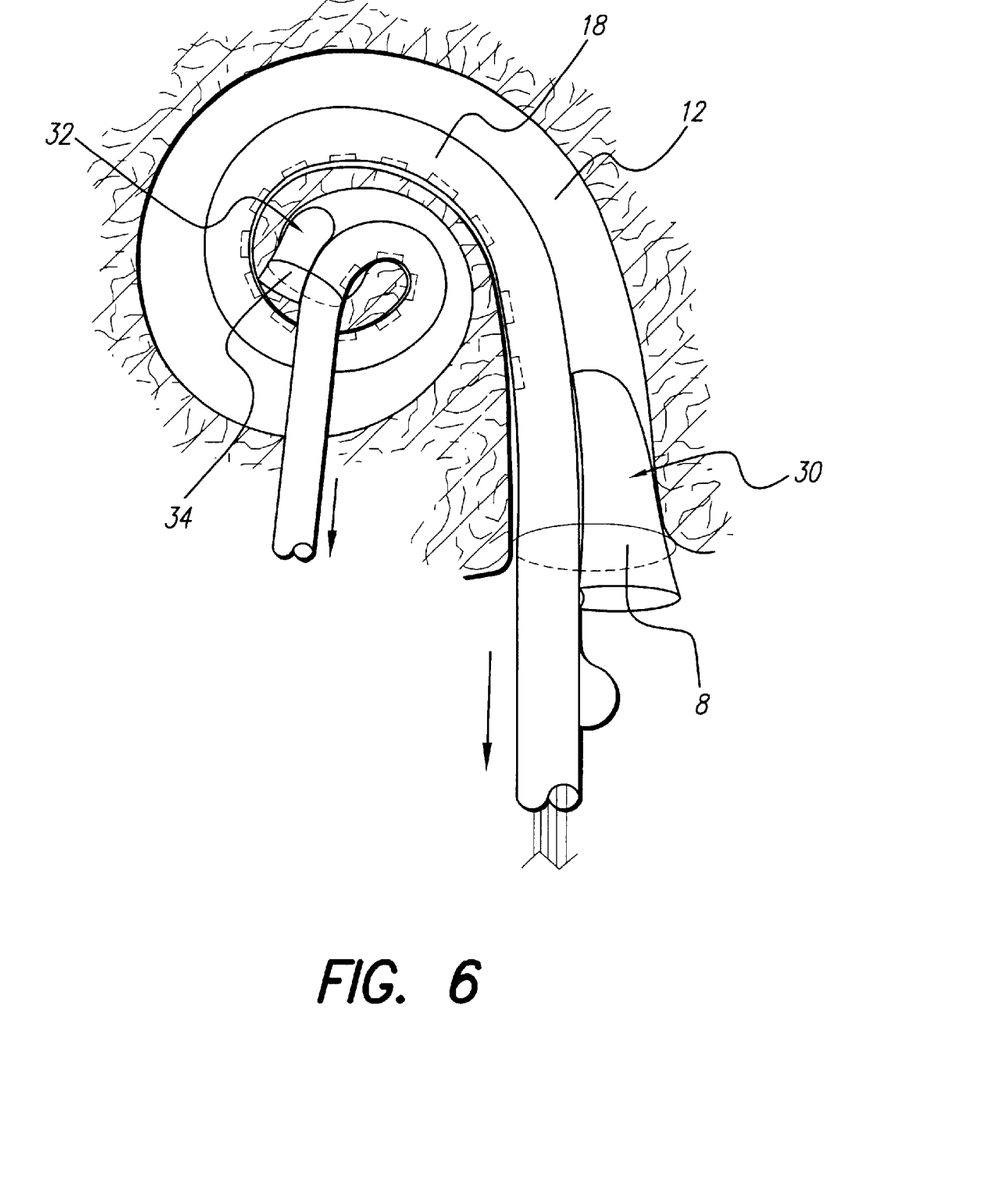
FIG. 6 depicts the final position of the electrode array within the cochlea after a gentle pulling force has been applied to both ends of the electrode array.

Once the electrode array 18 is in place within the scala tympani, the electrode array 18 is gently pulled from both ends putting the electrode array 18 into tension, as shown in FIG. 6. Tension on the electrode array 18 results in the electrode array 18 moving to the inside radius of the scala tympani 12. The result is that the electrodes 22 are placed in close proximity to the ganglion cells 14, which proximity results in efficient stimulation of the ganglion cells 14. Without releasing the tension on the electrode array 18, the first wedge 30 is inserted into the basal cochleostomy 8, and the second wedge 32 is inserted into the apical cochleostomy 34. Following successful positioning of the electrode array 18 within the scala tympani 12, the leading section 20 is cut from the electrode array 18 and discarded.

Figure 7:
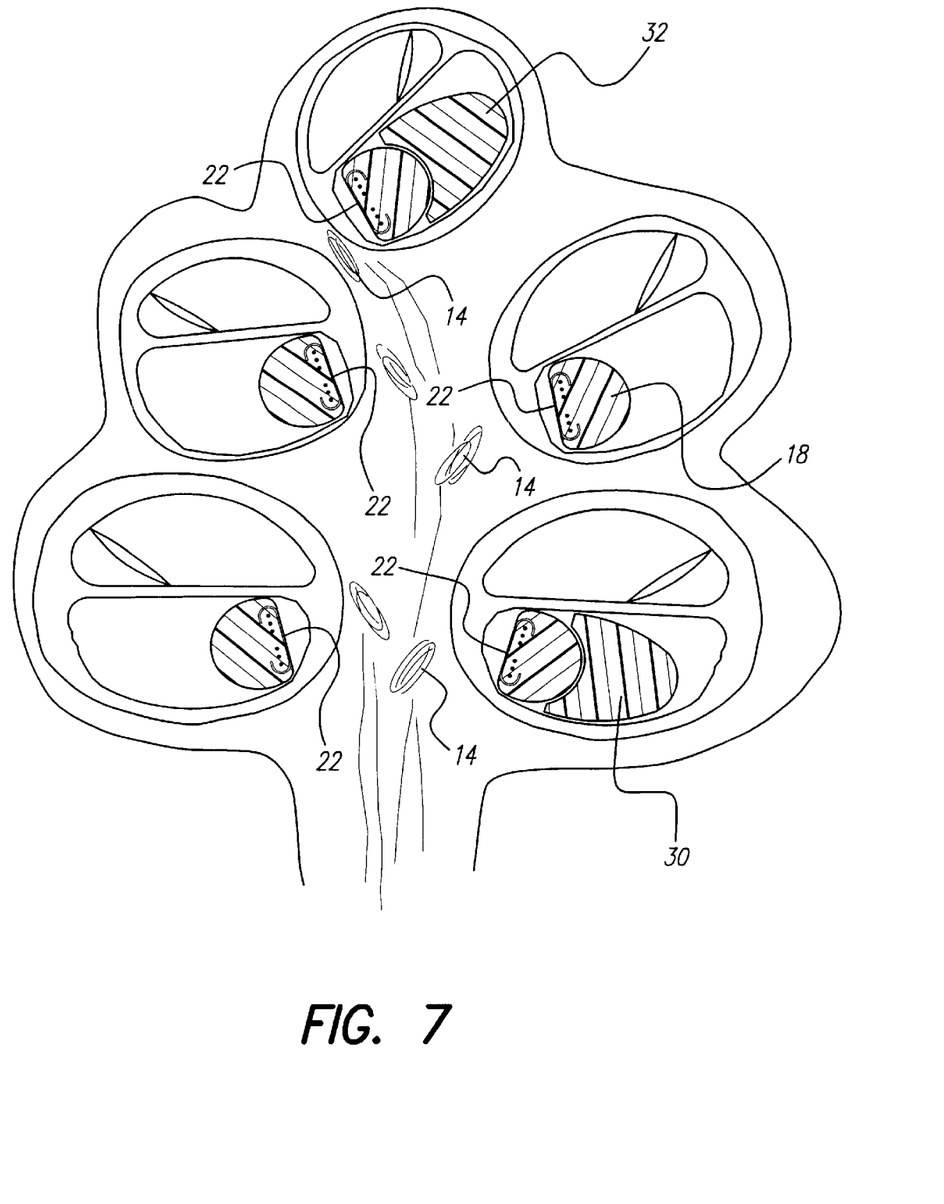
FIG. 7 illustrates the preferred position of the electrodes of the electrode array relative to the ganglion cells.

Turning to FIG. 7, the final position of the electrode array 18 within the scala tympani 12 is shown. The first and second wedges are shown in place, and the electrodes 22 are shown proximal to the ganglion cells 14.

Figure 8:
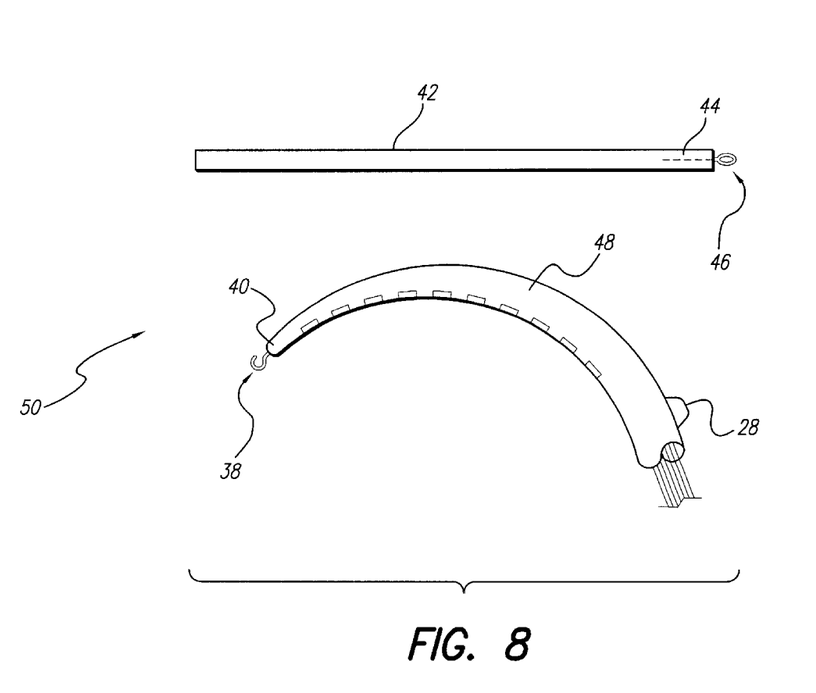
FIG. 8 depicts a second embodiment of an electrode assembly made in accordance with the invention.

A second embodiment of the electrode assembly of present invention is shown in FIG. 8. The second electrode assembly 50 comprises, a second electrode array 48 and a second leading section 42 removably attachable to the second electrode array 48. Further, the second electrode array 48 comprises an array forward end 40 and an array hook 38 attached to the array forward end 40. The second leading section 42 includes an attaching end 44, and a leader loop 46 attached to the second leading section's attaching end 44. The method of insertion for this embodiment comprises two steps. First, the second leading section 42 is inserted (attaching end 44 first) through the apical cochleostomy 34. The second leading section 42 is then promoted through the scala tympani until the attaching end 44 reaches the basal cochleostomy 8. A micro hook 38 is then inserted through the basal cochleostomy 8 to engage the leader loop 46 and to pull the second leading section 42 through the basal cochleostomy 8.

In the second step, the array hook 38 is connected to the leader loop 46. The second leader section 42 is then gently pulled back through the scala tympani 12 pulling the second electrode array 48 with the second leading section 42 until the depth marker 28 reaches the basal cochleostomy 8. The second leading section 42 is then detached from the second electrode array 48. The second electrode array 48 is then put in tension and fixed by the first and second wedges as described above for the first embodiment.

The methods of insertion for both the first embodiment and second embodiment assume that the electrode array must be inserted through the basal cochleostomy 34. In general, electrode arrays used for cochlear stimulation have been tapered, and fit best when inserted from the basal end of the cochlea. The tapering is beneficial in positioning the electrodes near the ganglion cells when using arrays known in the art. However, an electrode array and method of insertion in accordance with the present invention, allows the electrodes to be positioned in close proximity to the ganglion cells, and the taper is longer advantageous. If, for example, a constant diameter ring electrode array is used, the electrode array would not require insertion from the basal end of the scala tympani. That is, a constant diameter electrode array, allows the method of insertion described for both embodiments to be performed from either end of the scala tympani.

Preferred techniques of making an electrode array that are applicable to the present invention are described in Applicant Kuzma's U.S. Pat. No. 6,070,105; 6,129,753; and 6,038,484, which patents are incorporated herein by reference. These patents teach the construction of electrode arrays that resist twisting and are precurved, or readily curveable, to better define the electrode contact orientation toward the ganglion cells after insertion. If the electrode array used with the present invention uses other than banded electrodes, the arrays described by the '105, '753 and '484 patents may provide better targeting of the intended ganglion cells than do other electrode arrays.

While the invention herein disclosed has been described by means of specific embodiments and applications thereof, numerous modifications and variations could be made thereto by those skilled in the art without departing from the scope of the invention set forth in the claims.

What is claimed is:

1. An implantable cochlear electrode assembly comprising:
   an electrode array implantable within a cochlea having an array distal end; and
   a leading section having a forward end and a rearward end, and wherein the rearward end of the leading section is attached to said electrode array distal end;
   wherein said forward end of said leading section is insertable into the cochlea through a first cochleostomy, and further wherein said leading section is promotable through the cochlea to a second cochleostomy, at which second cochleostomy said forward end is extractable from the cochlea, and further wherein said leading section is pullable through said second cochleostomy, resulting in said electrode array being positioned within the cochlea for stimulation of ganglion cells.

2. The electrode assembly of claim 1, wherein said electrode array, when implanted in a cochlea, extends from a base of the cochlea to an apex of the cochlea.

3. The electrode assembly of claim 2, further wherein said electrode array is placed in tension within the cochlea by pulling on the ends of said electrode array at said first and second cochleostomies, thus positioning said electrode array in close proximity to the ganglion cells of the cochlea.

4. The electrode assembly of claim 3, wherein said electrode array is held in tension by a first wedge insertable at the first cochleostomy and a second wedge insertable at the second cochleostomy.

5. The electrode assembly of claim 4, wherein said electrode array and said leading section are integrally joined as a single piece, and further wherein said leading section is detachable from said electrode array upon the positioning of the electrode array within the cochlea.

6. The electrode assembly of claim 5, wherein the electrode array is adapted to be implanted within the scala tympani of the cochlea.

7. The electrode assembly of claim 6, wherein the first cochleostomy comprises a basal cochleostomy, and the second cochleostomy comprises an apical cochleostomy.

8. An implantable cochlear electrode assembly comprising:
   an electrode array including an array forward end and an array hook attached to said forward array end, and wherein said electrode array is adapted for implantation within a cochlea; and
   a leading section including a forward end and further including a leader loop attached to said forward end;
   wherein said forward end of said leading section is adapted for insertion into the cochlea through a first cochleostomy, and further wherein said leading section is promotable through the cochlea to a second cochleostomy, at which second cochleostomy said forward end is extractable from the cochlea, and further wherein said leader loop is attachable to said array hook, and further wherein said leader section may be pulled back through said second and first cochleostomies with said electrode array attached, resulting in said electrode array being positioned within the cochlea for stimulation of ganglion cells.

9. The electrode assembly of claim 8, wherein said electrode array, when implanted within the cochlea, extends from a base of the cochlea to an apex of the cochlea.

10. The electrode assembly of claim 9, further wherein said electrode array is placed in tension within the cochlea by pulling on the ends of said electrode array, thus positioning said electrode array in close proximity to the ganglion cells of the cochlea.

11. The electrode assembly of claim 10, wherein said electrode array is held in tension by a first wedge insertable at the first cochleostomy and a second wedge insertable at the second cochleostomy.

12. The electrode assembly of claim 11, wherein the electrode array is adapted for implantation within the scala tympani of the cochlea.

13. The electrode assembly of claim 12, wherein the first cochleostomy comprises an apical cochleostomy, and the second cochleostomy comprises a basal cochleostomy.

14. A method for implanting an electrode array for cochlear stimulation along the entire length of the cochlea comprising:
   drilling a basal cochleostomy and an apical cochleostomy;

inserting a forward end of a leading section of an electrode assembly through the basal cochleostomy, the electrode assembly including an electrode array with spaced-apart electrodes thereon;

promoting the leading section through the cochlea;

extracting the forward end of the leading section from the apical cochleostomy; and pulling the leading section and the attached electrode array through the cochlea until the electrodes of the electrode array are in the correct position for stimulation of the ganglion cells.

15. The method of claim 14 further including:

pulling both ends of the electrode array extending from the apical cochleostomy and the basal cochleostomy to position the electrodes against the inner radius of the cochlea.

16. The method of claim 15 further including:

inserting wedges at the basal cochleostomy and the apical cochleostomy to fix the position of the electrode array.

* * * * *